Jan. 8, 1974 A. W. FISCHER Plant Pat. 3,426
AFRICAN VIOLET PLANT
Filed Jan. 24, 1972
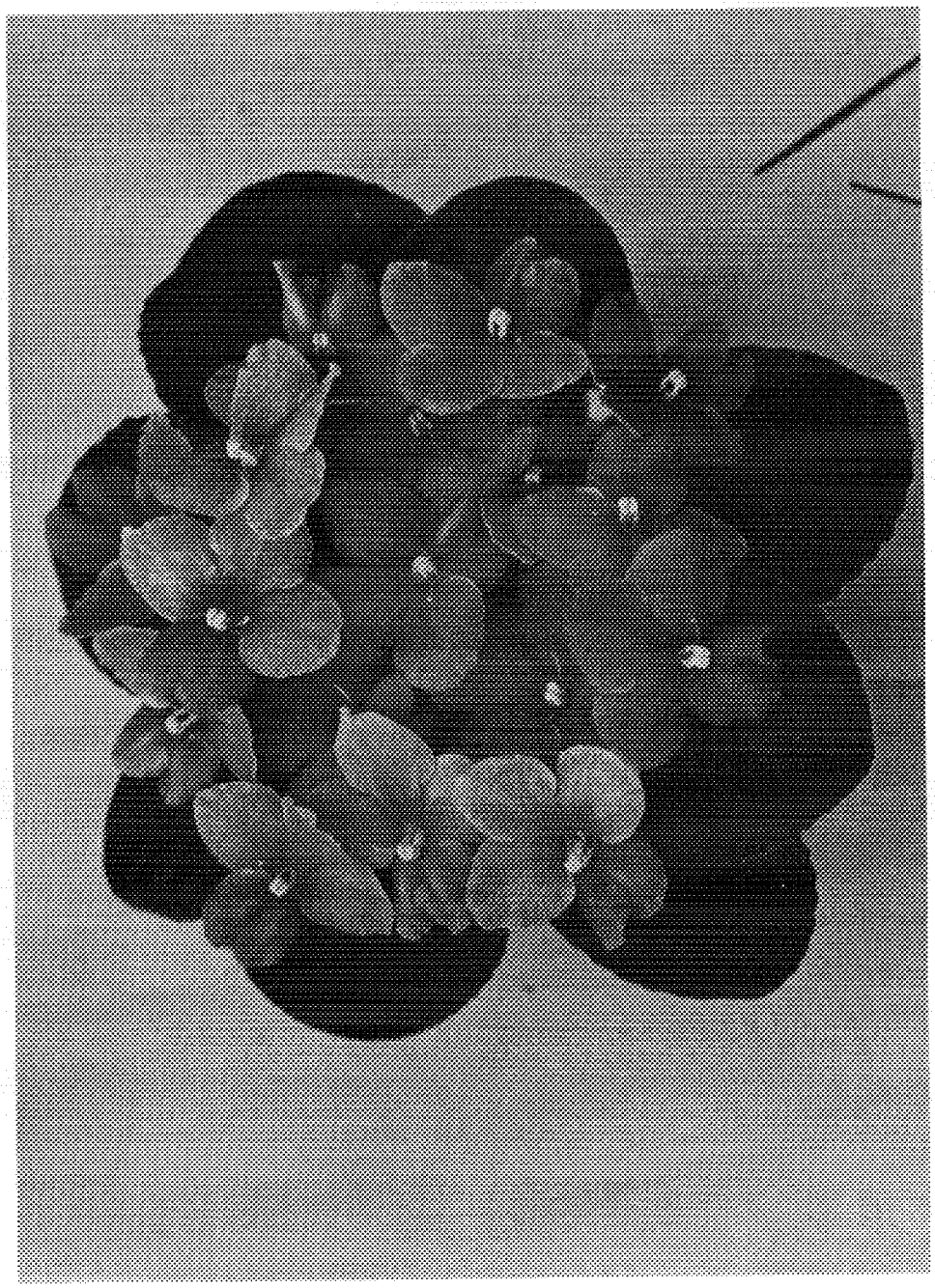

United States Patent Office

Plant Pat. 3,426
Patented Jan. 8, 1974

3,426

AFRICAN VIOLET PLANT

Arnold W. Fischer, Isernhagen, Germany, assignor to Geo. J. Ball, West Chicago, Ill.

Filed Jan. 24, 1972, Ser. No. 220,508
**Int. Cl. A01h *5/00***
U.S. Cl. Plt.—69 1 Claim

ABSTRACT OF THE DISCLOSURE

A new variety of African violet plant distinguished by the medium to large size of its delicate pink flowers which are carried on short peduncles branching from relatively long flower stalks which tend to spread laterally above relatively large, almost circular leaves carried on long, horizontally extending petioles to provide a sharply contrasting background for a bunched mass of the flowers.

BACKGROUND OF THE INVENTION

This new variety of African violet plant originated as a seedling developed by me at Isernhagen, Germany, where I have been conducting the culture and breeding of African violets for the purpose of developing improved varieties of the plants for the commercial market. The objects of my breeding efforts are to develop African violet plants which are more hardy and grow more vigorously and which blossom more profusely with attractive and pleasing colors. This variety was selected for test because of the delicate pink color of its blooms and the relatively low and spreading growth habit which appeared to display the blooms in a very attractive manner. Asexual propagation of this new variety under my direction, by means of leaf cuttings, at Isernhagen, Germany, has shown this plant to retain all of its original distictive characteristics and to do so from generation to generation. Commercial propagation of this new variety is now being carried on at West Chicago, Ill., U.S.A., by means of leaf cuttings and division of shoots.

DESCRIPTION OF THE DRAWING

This new variety of African violet plant is illustrated by the accompanying drawing which shows the form and color characteristics of the plant and its blooms and foilage, the color rendition being as nearly true as is reasonably possible to obtain by conventional photographic procedures.

DESCRIPTION OF THE NEW PLANT

The following is a detailed description of my new variety of African violet plant with color identification according to the Horticultural Colour Chart published by the Britsh Colour Council in collaboration with the Royal Horticultural Society of London, England.

*The plant*

Origin: Seedling
Parentage: *Seed parent.*—A double pink (unnamed and unpatented)
*Pollen parent.*—A single pink (unnamed and unpatented)
Classification: *Botanic—Saintpaulia ionantha*
*Commercial.*—African violet
Form: Compact potted plant (rosette arrangement)
Height: 2½ inches from base to top of flowers when in full bloom
Growth: Condensed and compact, fairly strong and tending to spread horizontally
Foliage:
*Quantity.*—abundant
*Size of leaf.*—2 to 2 7/16 inches long by 2 to 2⅜ inches wide

*Shape of leaf.*—Almost round with crenate margins
*Texture.*—Leathery and tough
*Aspect.*—Very tomentose
*Veins.*—Pinnate and very pronounced on under side. Veins do not connect at the leaf edges
*Color.*—Upper side—Ivy Green 0001060. Under side—Maroon 1030/3
*Petioles.*—1¾ to 2¼ inches long

*The bud*

Form: Generally globular or elliptical
Size: Average—3/16 to ¼ inch in diameter and ¼ inch in depth
Opening: Very slowly—5 weeks from visible bud to flower opening
Color: When petals unfurl—Mauve 633/2
Sepals: Hooded over bud for a very short time
*Form.*—Sepals are branched, upstanding and spear-shaped
*Color.*—Inside—Maroon 1030. Outside—Sage Green 000861
Calyx:
*Shape.*—Splits to star shape
*Aspect.*—Smooth on inside and hairy on outside
Peduncle:
*Length.*—¼ to ½ inch on a flower stalk 1¼ inches to 2 inches long
*Strength.*—Flexible
*Aspect.*—Very tomentose
*Color.*—Maroon 1030

*The flower*

Blooming habit: Profusely and recurrent the year around with a tendency to bloom early
Size of flower: Variable but most are medium to large
*Diameter.*—1 to 1⅜ inches
*Depth.*—Mostly flat but many up to ⅝ inch
Borne: In cluster at end of flower stalk
Shape: Very open cup-shaped when bloom first opens changing to almost flat
Petalage: Number of petals—5, 3 noticeably larger than remaining 2
*Arrangement.*—Sympetalous
*Form.*—Rotate and bilaterally symmetrical with smooth edges
*Color.*—Face side—Petunia Purple 32/1. Reverse side—Mauve 633
*Texture.*—Soft
*Appearance.*—Slightly shiny on top side, very tomentose on under side
Peduncle: ¼ inch to ½ inch long for each flower at end of stalk, 1¼ inches to 2 inches long from base to penduncle
*Strength.*—Flexible and tends to be more horizontal than upright
*Color.*—Maroon 1030
Discoloration after full bloom: Color fades greatly
Effect of temperature: Hot environment fades flowers and suppressed flowering. Plant thrives in mild temperature and 80 to 90% relative humidity.
Fragrance: Very faint
Lasting quality: 10 to 14 days from flower opening
Persistence: Blossoms hang on and dry on the stalk

*Reproductive organs*

Stamens:
*Anthers.*—Arrangement—basifixed. 2 in number, each 1/16 inch long and composed of 2 anther cells which give the appearance of 4 anthers in each blossom
*Filaments.*—3/16 inch to ¼ inch long. Color—Sap Green 62/2

*Pollen color.*—White
Pistils: One in number, 3/8 inch long
Stigmas: Color—Mauve 633/1
Styles: 5/16 inch long and Mauve 633/1 in color
Ovaries: Superior and tomentose with a yellow ring at the base of ovary The principal distinctions of this new variety of African violet plant are to be found in the distinctive display of the medium large flowers which vary in form from bell-shaped to substantially flat and which are borne on very short peduncles at the end of a relatively long stalk. The plant is also distinguished by the arrangement of its foliage with almost round leaves carried on very long petioles which project the leaves horizontally outward leaving the center of the plant occupied by the mass of flowers which in overall aspect presents a relatively low but wide spreading display. This plant is more vigorous than its parents with abundant foliage and profuse production of blossoms.

I claim:

1. This new variety of African violet plant, substantially as herein shown and described, characterized by its abundant foilage and relatively large leaves of almost round shape carried on long petioles, by the extraordinary range of flower shapes which vary from bell-shape to substantially flat, and by the very short flower peduncles carried on an outwardly-inclined lower stalk.

No references cited.

ROBERT E. BAGWILL, Primary Examiner